United States Patent [19]

Neri et al.

[11] 4,161,540

[45] Jul. 17, 1979

[54] ANTIANDROGENIC AGENTS AND METHODS FOR THE TREATMENT OF ANDROGEN DEPENDENT DISEASE STATES

[75] Inventors: Rudolph O. Neri, Hawthorne; John G. Topliss, West Caldwell, both of N.J.

[73] Assignee: Schering Corporation, Kenilworth, N.J.

[21] Appl. No.: 838,606

[22] Filed: Oct. 3, 1977

Related U.S. Application Data

[60] Continuation of Ser. No. 725,822, Sep. 23, 1976, which is a division of Ser. No. 505,116, Sep. 11, 1974, Pat. No. 3,995,060, which is a continuation-in-part of Ser. No. 265,655, Jun. 20, 1972, abandoned, which is a continuation-in-part of Ser. No. 146,461, May 24, 1971, abandoned, which is a continuation-in-part of Ser. No. 876,999, Nov. 14, 1969, abandoned, which is a continuation-in-part of Ser. No. 734,854, Jun. 6, 1968, abandoned, which is a continuation-in-part of Ser. No. 573,836, Aug. 22, 1966, abandoned.

[51] Int. Cl.$^2$ .......................................... A61K 31/165
[52] U.S. Cl. .................................................... 424/324
[58] Field of Search ......................................... 424/324

*Primary Examiner*—Jerome D. Goldberg
*Attorney, Agent, or Firm*—Raymond A. McDonald

[57] ABSTRACT

This application relates to certain 4'-substituted and to 3',4'-disubstituted anilides, to methods for their preparation and to methods for their use as antiandrogens. These substituted anilides are useful in the treatment of androgen dependent disease states, such as benign prostatic hypertrophy, hirsutism, acne and the like.

16 Claims, No Drawings

ANTIANDROGENIC AGENTS AND METHODS FOR THE TREATMENT OF ANDROGEN DEPENDENT DISEASE STATES

This application is a continuation of our co-pending application Ser. No. 725,822, filed Sept. 23, 1976, which in turn is a divisional of application Ser. No. 505,116, filed Sept. 11, 1974 (now U.S. Pat. No. 3,995,060) which in turn is a continuation-in-part of our co-pending application Ser. No. 265,655, filed June 20, 1972 (now abandoned), which in turn, is a continuation-in-part of application Ser. No. 146,461, filed May 24, 1971, (now abandoned), which in turn, is a continuation-in-part of application, Ser. No. 876,999, filed Nov. 14, 1969 (now abandoned), which in turn, is a continuation-in-part of application, Ser. No. 734,854, filed June 6, 1968 (now abandoned), which in turn, is a continuation-in-part of application, Ser. No. 573,836, filed Aug. 22, 1966 (now abandoned).

This invention relates to valuable therapeutically active chemical compositions belonging to the general class of substituted anilides and to the processes for making and using such therapeutically effective compositions.

The invention sought to be patented, in one of its composition of matter aspects, is described as residing in the concept of a therapeutically effective quantity of a substituted anilide in admixture with a pharmaceutical carrier.

The tangible embodiments of this invention are more specifically described as substituted anilides of the structural formula:

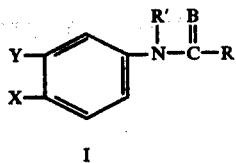

I wherein X is a member of the group consisting of nitro, trifluoromethyl, chloro, bromo and iodo; Y is a member of the group consisting of hydrogen, halogen, nitro, carboxy, lower alkyl, hydroxy, lower alkoxy, lower alkanoyl, lower alkanoyloxy, polyfluoroloweralkoxy, lower carbalkoxy, polyfluoroloweralkyl, and trifluoromethylthio, with the proviso that when Y and R' are both hydrogen, X is other than iodo; B is a member of the group consisting of sulfur and oxygen; R' is a member of the group consisting of hydrogen and alkyl having less than 5 carbon atoms; and R is cyclopropyl, cyclobutyl or branched chain alkyl having up to 8 carbon atoms.

As used herein the term lower alkyl embraces alkyl groups having up to about 5 carbon atoms, including branched chain and cyclic alkyl groups. Lower alkyl groups having from 1 to 3 carbon atoms are preferred. Similarly, the term polyfluoroloweralkyl embraces lower alkyl groups wherein at least two of the hydrogens are replaced by fluorine. Therefore, unless stated otherwise the term embraces both partially fluorinated and perfluoro groups; the preferred polyfluoroloweralkyl groups being those having from 1 to 3 carbon atoms. The term branched chain alkyl group, as used herein, means monovalent alkyl groups having substituent alkyl groups and includes doubly branched alkyl groups wherein the substituents are on different carbon atoms.

The term lower alkanoyl and loweralkoxy also have the 1 to 5 carbon chain length limitation and the same 1 to 3 carbon chain preference. Exemplary of the foregoing groups are methyl, ethyl, isopropyl, cyclopropyl, cyclobutyl; difluoromethyl, trifluoromethyl, $\alpha,\alpha$-difluoroethyl, $\beta,\beta,\beta$-trifluoroethyl; formyl, acetyl, propionyl, isobutyryl, methoxy, ethoxy, isopropoxy, t-butoxy and the like.

The substituted carboxanilides of this invention may be prepared by the condensation of an appropriated X, Y, R'-substituted aniline with an acyl halide, the condensation being effected by heating a mixture of at least equimolar quantities of the reactants in the presence of an acid acceptor. Preferably the heating of the reactants takes place in a solvent at elevated temperatures up to about the reflux temperature of the reaction mixture. Suitable solvents include such organic compounds as benzene, xylene, diethylether, pyridine and triethylamine. Suitable acid acceptors include triethylamine, pyridine, alkali metal salts, such as sodium and potassium carbonates and the like. If desired, the reaction solvent itself may serve as the acid acceptor, such as when the triethylamine and pyridine solvents are employed. The condensation reaction proceeds rapidly and at the completion thereof the reaction mixture is admixed with a dilute mineral acid and cooled. The desired product is then removed from the aqueous mixture by extraction with water immiscible solvents such as diethyl ether, toluene, chloroform, ethyl acetate and the like. After appropriate water-washings, the product is isolated by evaporation of the solvent, and the product then further purified by the usual techniques, such as by recrystallization.

The following reaction may be summarized by the following schematic representation:

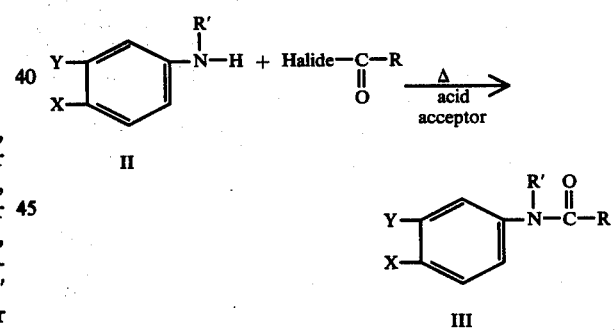

wherein X, Y, R' and R are as previously defined.

The thio analogs of the substituted carboxanilides may be prepared by a replacement reaction using the appropriately substituted carboxanilide (III) starting material. For example, to obtain the desired thioanilide the appropriate substituted carboxanilide is refluxed in the presence of $P_2S_5$ in a solvent such as toluene yielding the desired thio derivative of the carboxanilide starting material. This reaction is depicted as follows:

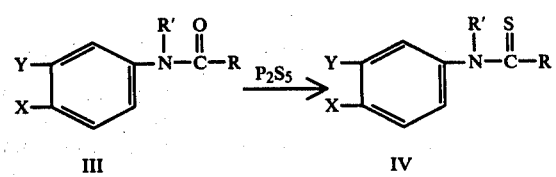

wherein X, Y, R' and R are as previously defined.

Alternatively, thioanilides may be directly prepared by condensing an appropriately X, R, R' substituted aniline with such reactants as (1) a dithioacid or (2) a dithioester; these condensations being conducted according to the usual and well known techniques. These condensation reactions may be schematically represented by the following:

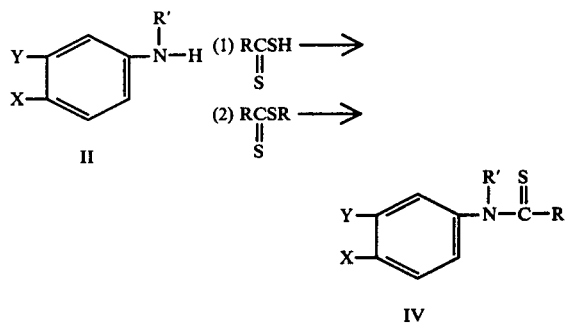

wherein X, Y, R' and R are as previously defined.

In those instances wherein the Y-substituent (i.e. the substituent meta to the anilide group) is a polyfluoroloweralkyl group other than a perfluoro compound, such as difluoromethyl or α,α-difluoroethyl, the compound bearing such substituent may be prepared by heating m-nitrobenzaldehyde or m-nitroacetophenone with sulfur tetrafluoride under pressure to form the corresponding difluoro compound. Hydrogenation of the nitro group affords the m-substituted aniline which may be acylated as described above. The X-substituents (i.e. the nitro, trifluoromethyl, chloro, bromo and iodo substituents) may be prepared by aromatic substitution reactions known to the art. Where the desired R'-group of the foregoing substituted anilides is other than hydrogen, it is prepared by subjecting the substituted anilide to standard alkylation procedures. The thus formed R'-substituted anilide is thereafter treated as described above to yield the corresponding thioanilide.

The foregoing reactions may be summarized by the following schematic representation:

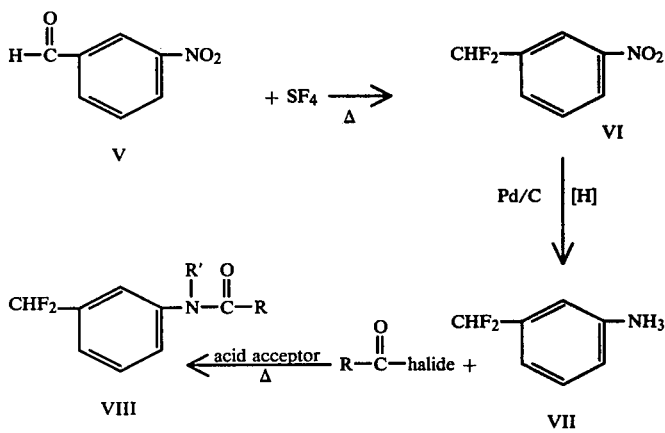

wherein R is as previously defined and R' is hydrogen.

In these instances wherein the desired Y-substituent is a trifluoromethylsulfoxy group, the compounds may be prepared by oxidation of the corresponding para-X-substituted trifluoromethylthioanilide. The oxidation may advantageously be effected by the use of such oxidizing agents as chromic acid, nitric acid, hydrogen peroxide, organic peracids or the like. Exemplary of such peracids are m-chloroperbenzoic acid, peracetic acid, monoperphthalic acid or the like. In general, m-chloroperbenzoic acid is preferred because of the ease with which the oxidation may be stopped at the sulfoxide stage when the reagent is used.

The foregoing reaction is depicted by the following schematic representation:

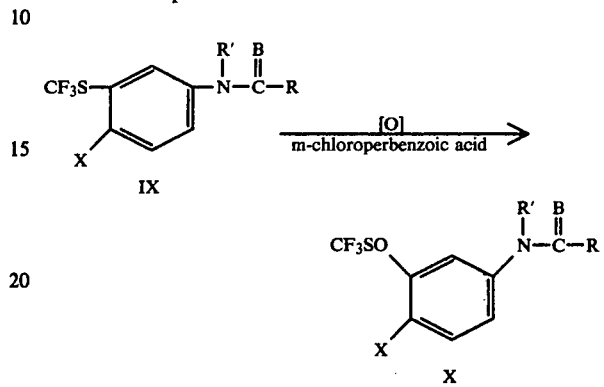

wherein X, B, R and R' are as previously defined.

In those instances wherein the desired Y-substituent is the trifluoromethylsulfonyl group, the compounds may be prepared by acylating the appropriate para-X-substituted meta trifluoroethyl sulfonylaniline to form the corresponding anilide as shown below:

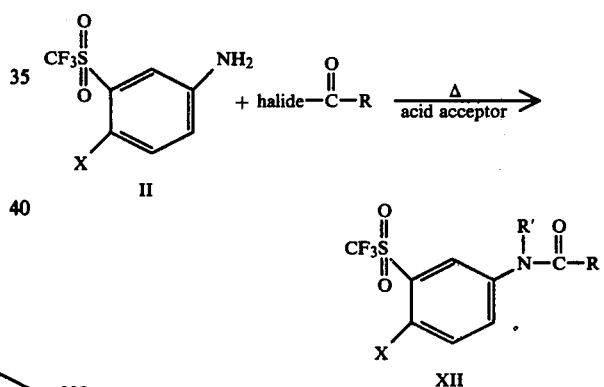

wherein X and R are as previously defined and R' is hydrogen. Compound XII may be methylated under standard conditions to yield the R'-methyl analog. Further, either the methylated or non-methylated compound may be treated as described above to yield the corresponding thioanilide.

Within the purview of the above-described compound are included the novel substituted anilides described below:

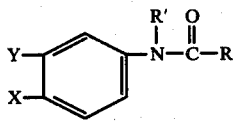

X, Y, R, and R' are defined under (a), (b) and (c) as follows:

(a) X is nitro; Y is a member of the group consisting of bromo, iodo, nitro, hydroxy, carboxy, lower alkyl, lower carbalkoxy, lower alkanoyl, lower alkanoyloxy, lower alkoxy, polyfluoroloweralkoxy, trifluoromethylthio, and polyfluoroloweralkyl excluding trifluoromethyl; R' is a member of the group consisting of hydrogen and alkyl having less than 5 carbon atoms; R is a member of the group consisting of cyclopropyl, cyclobutyl or branched chain alkyl having up to 8 carbon atoms; provided that when R is a doubly branched chain alkyl group of from 5 to 8 carbon atoms, Y may also be trifluoromethyl.

(b) X is a member selected from the group consisting of bromo and iodo; Y is trifluoromethyl; R' is a member of the group consisting of hydrogen and alkyl having less than 5 carbon atoms; and R is a member of the group consisting of cyclopropyl, cyclobutyl and branched chain alkyl having up to 8 carbon atoms.

(c) X is a member of the group consisting of bromo, iodo and trifluoromethyl; Y is a member of the group consisting of iodo, bromo, nitro, hydroxy, carboxy, lower alkoxy, polyfluorolower alkoxy, lower alkanoyl, lower alkanoyloxy, lower carbalkoxy, trifluoromethylthio, and polyfluoroloweralkyl excluding trifluoromethyl, with the proviso that when X is bromo Y must be other than bromo; R' is a member of the group consisting of hydrogen and alkyl having less than 5 carbon atoms; and R is a member of the group consisting of cyclopropyl, cyclobutyl or branched chain alkyl having up to 8 carbon atoms.

The carboxanilides of formula I may also be prepared by an appropriate method selected from the following known reactions for the preparation of amides:

(a) pyrolysis of the isoalkylcarboxylate or cycloalkylcarboxylate salt of an amine of formula II; however, this method is not recommended for preparing those compounds wherein Y is an alkanoyloxy group or a lower carbalkoxy group;

(b) Beckman rearrangement of an oxime or O-acyl derivative thereof of the formula:

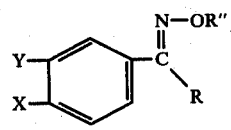

wherein R, X and Y are as defined above, and R'' is hydrogen or an acyl group, e.g., acetyl, mesyl or tosyl.

This process yields carboxanilides of the formula I in which R' is hydrogen;

(c) Schmidt reaction between a ketone of the formula:

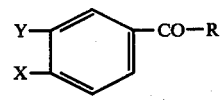

wherein R, X and Y are as defined above, and a substantially equimolar quantity of hydrazoic acid in the presence of a strong acid, and isolation of the desired product of the formula I. This process is not recommended for preparing those compounds wherein Y is a lower carbalkoxy group.

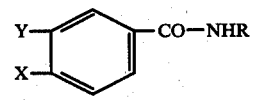

This process yields carboxanilides of the formula I in which R is hydrogen;

(d) A polonovski type reaction between a methylalkyl anilide oxide of the formula:

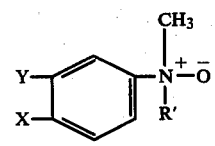

wherein X, Y and R' are as defined above, and a reactive derivative of a branched chain or a cyclic carboxylic acid, such as an isopropylcarboxylic acid or of cyclopropylcarboxylic acid, preferably the anhydride or chloride. This process yields carboxanilides of the formula I in which R' is alkyl;

(e) Reductive acylation of a nitrobenzene derivative of the formula IIa

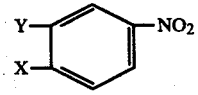

(IIA)

wherein X and Y are as defined above, by means of a cycloalkylcarboxylic acid or a branched chain carboxylic acid or a reactive derivative thereof, e.g., the anhydride, in the presence of a reducing metal, e.g., zinc. This process yields carboxanilides of the formula I in which R' is hydrogen. However, it is inoperable for preparing those compounds wherein either Y or X are a nitro group;

(f) Oxidation of a compound of the formula:

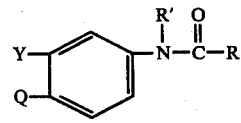

wherein Y, R and R' are as defined above, and Q represents —NH₂, NHOH or —NO. The oxidation is preferably effected by means of a peroxide, e.g., hydrogen peroxide, trifluoro per acetic acid, or persulfuric acid, although other oxidizing agents such as permanganates and nitric acid can be used when Q is —NO. The process yields carboxanilides of the formula I in which X is nitro. The process is not recommended for preparing these compounds wherein Y is a member of the group consisting of hydroxy, lower alkanoyloxy, lower alkanoyl, trifluoromethylthio, and trifluoromethylsulfoxy;

(g) Reduction of an anilide of the formula:

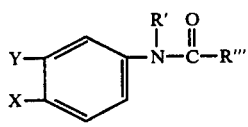

wherein X, Y and R' are as defined above, and R''' represents an isopropenyl or cyclopropenyl radical, preferably with hydrogen and a catalyst, e.g. platinum. This procedure is not recommended for preparing compounds wherein X or Y is nitro.

(h) Amide exchange reaction wherein an anilide is reacted with isopropylcarboxylic acid or cyclopropylcarboxylic acid under conditions favouring formation of the isopropylcarboxanilide or cyclopropylcarboxanilide, e.g., by heating with a large excess of isopropylcarboxylic acid or of cyclopropylcarboxylic acid, or under reaction conditions designed to remove the acid moiety of the starting anilide from the reaction mixture: e.g.

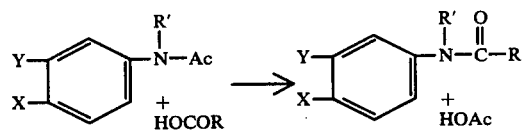

wherein X, Y, R and R' are as defined above, and Ac is an acyl group. The starting anilide can be chosen to yield an acid AcOH which is removed from the reaction mixture and so favour formation of the desired anilide. A volatile acid AcOH (such as acetic or formic acid) can be distilled out of the reaction mixture. When in the starting anilide Y is hydroxy, the product must be hydrolyzed to remove the acyl radical of the higher boiling carboxylic acid. In those instances wherein Y is in the starting anilide is a lower alkanoyloxy group, the product must be hydrolyzed to remove the acyl radical of the higher boiling carboxylic acid and re-esterified to yield the desired lower alkanoyloxy compound;

(i) Alkylation of an isocyanate of the formula:

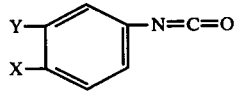

or of a carbamyl halide of the formula:

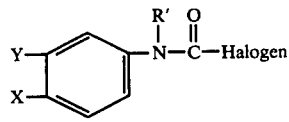

wherein X, Y and R' are as defined above, with an organo-metallic compound R—M, where R is as defined above, and M is a metal-containing moiety, preferably Mg-halogen. The isocyanate yields carboxanilides of the formula I wherein R' is hydrogen. This process is not recommended for preparing those compounds wherein X is a nitro group or wherein Y is hydroxy, carboxy, nitro or lower alkanoyl;

(j) Isomerization of an N-halo-anilide of the formula, in an Orton type rearrangement

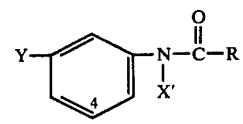

wherein Y and R are as defined above, and X' is halogen, chlorine, bromine or iodo, by heating (e.g., to 100°–300° C.) or by photolysis, whereby the halogen atom X' migrates to the 4-position. Further, the N-haloanilide intermediate may be heated in the presence of HX'' to afford X'' in the 4-position. X'' does not necessarily have to the the same as X'. This process yields carboxanilides of the formula I wherein R' is hydrogen and X is halogen;

(k) Replacement of an activated halogen atom in an appropriately substituted halobenzene by the amido group —NR' CO—R by reaction of the halobenzene with an amide NHR' —CO—R in the presence of a strong base, e.g., sodium hydride or sodamide, and an inert solvent, e.g., dimethylformamide or dimethylsulfoxide:

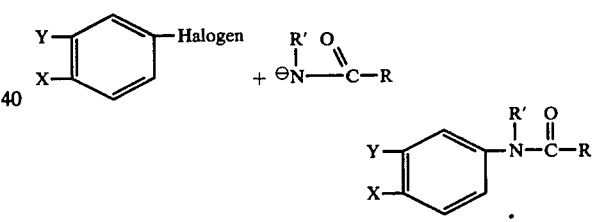

wherein Y, R' and R are as defined above, and X is peferably a nitro group. Y is preferably a hydrogen atom or a trifluoromethyl group, and the halogen atom is preferably chlorine, bromine or fluorine;

(l) Removal of a protecting group Pg from a compound of the formula:

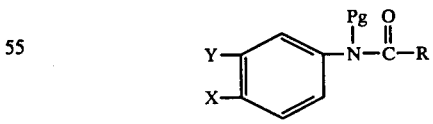

wherein X, Y and R are as defined above. The protecting group Pg is preferably one which can be removed by hydrogenolysis, e.g., a benzyl or a carbobenzoxy group. This process yields carboxanilides of the formula I wherein R' is a hydrogen atom. The process is not recommended for preparing those compounds wherein either X or Y is a nitro group. The protecting group (Pg) may also be one that can be removed by a mild hydrolysis such as a t-butyl carbonyloxy group

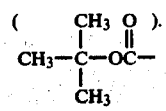

In this case, either or both X and Y may be a nitro group. However, when Y is a lower alkanoyloxy group, the product of the hydrolysis may require re-esterification.

(m) Elimination of a substituent Z from the benzene ring of a compound of the formula:

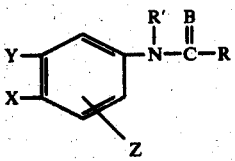

wherein X, Y, R', R and B are as hereinbefore defined. Z is preferably as —NH₂ group, which is eliminated by diazotization and reduction under standard conditions. Reduction can be effected for example with alcohol or hypophosphorous acid. This procedure is not recommended for preparing those compounds wherein Y is hydroxyl.

(n) Introduction of a substituent X into a compound of the formula:

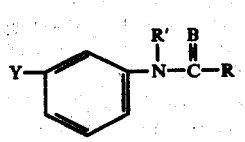

especially when X is chlorine, bromine, iodine or nitro, by standard methods of halogenation or nitration.

(o) Replacement of the —NH₂ group of a compound of one of the following formulae:

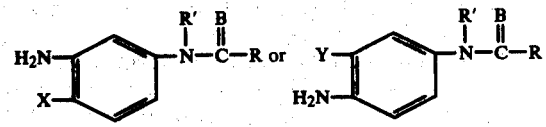

by Y or X respectively, when the group replacing the —NH₂ group is a halogen atom, by standard methods (including diazotization and replacement of the diazonium group by means of a Sandmeyer reaction to introduce chlorine or bromine, or by using a soluble metal iodide such as potassium iodide to introduce iodine). This procedure is not recommended for preparing those compounds wherein Y is hydroxyl.

The processes designated (e), (h), (i), and (j) set forth above for the preparation of carboxanilides are also feasible for the preparation of the thio anilides, with substitution of the appropriate sulfur analogs of the oxygen-containing reactants.

The preparation of the compounds of formula I is illustrated by the following specific examples.

EXAMPLE 1

4'-Nitro-3'-trifluoromethylisobutyranilide

To a stirred, cooled solution of 100 g. of 4-nitro-3-trifluoromethylaniline in 400 ml. of pyridine, slowly and in a dropwise fashion, add 54 g. of isobutyrylchloride and then heat the reaction mixture on a steam bath for 1.5 hours. Cool and pour the resulting mixture into ice-water, filter and water-wash the crude anilide, crystallize the product of this example from benzene to obtain analytically pure material, m.p. 111.5°–112.5° C.

Similarly by substituting the 4-nitro-3-trifluoromethylaniline reactant with equivalent quantities of the appropriate R', X, Y-aniline (as defined above) reactants, and by substantially following the foregoing procedure, there is produced the corresponding X,Y-isobutyranilide.

The isobutyrylchloride reactant may be replaced with equivalent quantities of cyclopropyl carbonyl chloride or a derivative which is convertible thereinto, and by following substantially the same procedure of this example there is produced the desired cyclopropyl carbonyl derivative.

EXAMPLE 2

4'-Bromo-3'-trifluoromethylisobutyranilide

To a stirred, cooled solution of 15.0 g. of 4-bromo-3-trifluoromethylaniline is 75 ml. of dry pyridine add 6.8 g. of isobutyrylchloride and heat the resulting mixture at 70° C. for 2 hours. Allow the reaction mixture to cool to room temperature and then pour the mixture into 600 ml. of ice-water, filter and dry the precipitate which is recrystallised from 1:1 petroleum etherdichloromethane to yield 4'-bromo-3'-trifluoromethylisobutyranilide, m.p. 126.5°–128° C.

EXAMPLE 3

4'-Iodo-3'-trifluoromethylisobutyranilide

A. 4'-Amino-3'-trifluoromethylisobutyranilide

Hydrogenate, at approximately 3 atmospheres, a mixture of 8.3 g. of 4'-nitro-3'-trifluoromethylisobutyranilide in 100 ml. of ethanol containing 0.5 g. of 5% palladium on charcoal. Filter and remove the solvent, obtaining 4'-amino-3'-trifluoromethylisobutyranilide, m.p. 114.5°–116° C.

B. 4'-Iodo-3'-trifluoromethylisobutyranilide

To a solution of 23.0 g. of 4'-amino-3'-trifluoromethylisobutyranilide in 150 ml. of glacial acetic acid and 100 ml. of water, while maintaining the mixture temperature at 10°–20° C., slowly add 17 ml. of concentrated sulfuric acid, cool the resulting mixture to about 0° C. and slowly add 8.5 g. of sodium nitrite in 15 ml. of water maintaining the temperature of the reaction at about 0° C. for 30 minutes. Add 50 g. of potassium iodide in 150 ml. of water and stir the resulting mixture for 1 hour. Filter, water-wash and dissolve the precipitate in 200 ml. of ether and remove the iodine by washing with a 10% sodium sulfite solution. Dry, remove the solvent, and recrystallize from carbon tetrachloride, obtaining the compound of this example, m.p. 143°–145° C.

EXAMPLE 4

4'-Nitro-3'-trifluoromethylisobutyrthioanilide

Reflux a mixture containing 16.8 gm. of phosphorous pentasulfide and 25.5 g. of 4'-nitro-3'-trifluoromethylisobutyranilide in 100 ml. of toluene for 6.5 hours and then filter. Concentrate the filtrate and chromatograph the residue from 500 g. of silica gel, eluting with 2 liters of benzene. Concentrate the last 1.2 liters of eluate to 40 ml. and extract the concentrate with two portions of 25 ml. of 10% sodium hydroxide. Combine the basic extract, acidify with 75 ml. of 10% sulfuric acid and collect the analytically pure product of this example, m.p. 74°–76° C.

EXAMPLE 5

4'-Nitro-3'-($\alpha,\alpha$-difluoroethyl)-isobutyranilide (a) 3-($\alpha,\alpha$-Difluoroethyl)-Nitrobenzene Heat 200 g. of m-nitroacetophenone and 520 g. of sulfur tetrafluoride in an autoclave at 100° C. for three hours and at 150° C. for twelve hours. Cool the mixture and dissolve the mass in chloroform. Wash the chloroform solution with an aqueous sodium hydroxide solution. Remove the solvent and obtain the product of this step by distillation (b.p. 65°–75° C./0.3 mm). Crystallize the distillated from petroleum ether at sub-zero temperature to obtain 3-($\alpha,\alpha$-difluoroethyl)-nitrobenzene.

EXAMPLE 6

4'-Nitro-3'-(trifluoromethylsulfoxy)-isobutyranilide

Dissolve 7.6 g. of 4'-nitro-3'-trifluoromethylthioisobutyranilide in 80 ml. of chloroform at about 20° C. Add 14.6 g. of 85% m-chloroperbenzoic acid to the previously prepared solution while maintaining the temperature substantially constant. Permit the reaction to continue for four hours. Wash the reaction mixture with 10% sodium hydroxide and dry over sodium sulfate. Evaporate the solvent to obtain a solid product. Recrystallize the product from dichloromethane-hexane to obtain the compound of this example.

By replacing the isobutyrylchloride reactant used in the foregoing examples with an equivalent quantity of other branched chain or cyclic acylating agents (e.g. acyl anhydrides or acyl chlorides) such as cyclobutyl carbonyl chloride, 2,3-dimethylbutyrylchloride or the like; and by following substantially the procedures set forth in said examples the acyl derivatives of substantially all of the X,Y-disubstituted anilines defined by formula II may be prepared.

In a similar manner, by substituting the X,Y-disubstituted anilines set forth in the preceding examples with an equivalent quantity of other such anilines such as 3-bromo-4-nitroaniline, 3-trifluoromethoxy-4-bromoaniline, 3-nitro-4-bromoaniline, 3,4-dinitroaniline, 3-iodo-4-nitroaniline, 3-methyl-4-nitroaniline or the like; and by following substantially the procedures set forth in said examples substantially all of the X,Y-disubstituted anilides defined by formula I may be prepared.

Exemplary of such X,Y-disubstituted anilides are the following:

3'-4'-dinitroisovaleranilide;
4'-chloro-3'-trifluoromethyl-cyclobutylcarbanilide;
3'-chloro-4'-iodocyclopropylcarbanilide;
3'-bromo-4'-nitro-3-methylvaleranilide;
3'-iodo-4'-trifluoromethylisobutyranilide;
3'-carboxy-4'-bromo-2,3-dimethylbutyranilide;
3'-carboxy-4'-nitro-2,3-dimethylbutyranilide;
3'-methyl-4'-nitro-3-methylcaproanilide;
3'-acetyl-4'-iodo-2,3-dimethylvaleranilide;
3'-acetyl-4'-nitro-2,3-dimethylvaleranilide;
3'-hydroxy-4'-nitro-2-methylbutyranilide;
3'-methoxy-4'-nitroisobutyranilide;
3'-ethyl-4'-trifluoromethyl-isobutyranilide;
3'-propionyloxy-4'-bromo-4-methylvaleranilide;
3'-propionyloxy-4'-nitro-4-methylvaleranilide;
3'-trifluoromethylthio-4'-nitro-2,3-dimethylvaleranilide;
3'-propyl-4'-chloroisobutyranilide;
3'-bromo-4'-trifluoromethylcyclopropylcarbanilide;
3'-bromo-4'-nitro-2,3-dimethylbutyranilide;
3'-nitro-4'-bromoisobutyranilide;
3'-iodo-4'-chloroisovaleranilide;
4'-nitrocyclopropylcarbanilide;
3'-carbethoxy-4'-chloro-2-ethylbutyranilide;
3'-carbethoxy-4'-nitro-2-ethylbutyranilide;
3'-hydroxy-4'-nitro-2,3-dimethylbutyranilide;
3'-propionyl-4'-trifluoromethyl-2,3-dimethylbutyranilide;
3'-propionyl-4'-nitro-2,3-dimethylbutyranilide;
4'-trifluoromethylisobutyranilide;
3'-trifluoromethyl-4'-nitro-isovaleranilide;
3'-trifluoromethyl-4'-nitro-2-methylbutyranilide;
3'-carboxy-4'-trifluoromethylisovaleranilide;
3'-carbomethoxy-4'-bromocyclopropylcarbanilide;
3'-fluoro-4'-nitroisobutyranilide;
3'-trifluoromethyl-4'-chloroisobutyranilide;
4'-nitroisobutyranilide;
3'-trifluoromethyl-4'-nitro-2-ethylbutyranilide;
3'-bromo-4'-nitroisobutyranilide;
3'-trifluoromethyl-4'-nitro-2,3-dimethylbutyranilide;
N-methyl-3'-trifluoromethyl-4'-nitroisobutyranilide;
N-methyl-3'-trifluoromethyl-4'-chloroisobutyranilide;
3'-trifluoromethyl-4'-bromoisobutyranilide.

In those instances wherein it is desired to prepare a X, Y-disubstituted anilide which is not specifically shown herein, such compound may be prepared by analogy processes known in the art.

By following substantially the procedure set forth in Example 4, the thio analogs defined by formula IV may be produced.

The tangible embodiment of the compositions of this invention possess the inherent general physical properties of being colorless or pale yellow and crystalline, exhibiting moderate melting points, and are substantially insoluble in water but soluble in common organic solvents such as aromatic hydrocarbons, halogenated hydrocarbons and the like.

The tangible embodiments of the compounds represented by formula I possess the inherent applied-use characteristics of exerting an anti-androgenic response when administered within the dose range of about 0.1 mg. to about 50 mg. per kg. of body weight per day and thus are useful in treating, alleviating and/or palliation of androgen-caused and/or androgen-dependent conditions such as benign prostatic hypertrophy, the Stein-Leventhal syndrone, idiopathic hirsutism, acne, and the like. Additionally, the antiandrogenic characteristics of the compounds of this invention have interesting veterinary-use application.

In those species afflicted with benign prostatic hypertrophy the frequency of the hypertrophic condition seems to increase with increasing age and thus represents a serious problem, even among older canine household pets. In general, hormone therapy, such as for example, administration of estrogenic substances, has not proved to be a particularly desirable treatment, not only because of the undesirable side effects due to the inherent properties of the estrogens, but also because such agents have not proved to be fully efficacious in providing meaningful remissions and cures. Surgical ablation, even though effective, is also not particularly desirable for in addition to the expected 2-3% mortality rate, many patients experience such non-fatal complications such as epididymitis, pneumonia, pyelonephritis, secondary resection, etc. Thus, the chemotherapeutic treatment of benign prostatic hypertrophy with concomitant absence of side effects induced by the anti-androgenic agent is also a goal long sought.

It has been determined by standard laboratory test procedures that the compounds of this invention produce marked remissions in cases of benign prostatic carcinoma without the undesirable effects elicited upon the administration of estrogens or complications inherent in any surgical procedures. Usually, depending upon the severity of the condition, a satisfactory therapeutic response is achieved in those mammal species having an adult body weight of approximately 70 kg. when 1 to 4 dosage units of a formed pharmaceutical formulation containing a compound of this invention is administered to the species. Thus a suitable dosage range for a 70 kilogram mammal is in the range of about 25 mg. to 500 mg. of the preferred active ingredients per day until symptomatic relief is obtained as ascertained by the attending diagnostician.

In addition to the aforementioned applied uses, the compounds of this invention (I) also are especially valuable for veterinary uses. For example, the administration of the compounds of this invention is useful in reducing androgen-caused odor normally associated with the meat of male animal species, in controlling and/or eliminating the birth of normal males, and for reducing the aggressive tendencies of the male animal species; these actions of course being dependent largely on the time of administration of the anti-androgenic agent.

As stated, the compounds of this invention may be used as chemical castrating agents in the veterinary field. It has been long known that male bovine and porcine species are not particularly suitable as meat producing animals. It is also known that the male animal grows at a faster rate, usually weighs more and produces a leaner carcass than does the corresponding female species. One attempt at converting the male into a more suitable commercial meat source has been by surgical castration (i.e. removal of the androgen source). However, this method has not been completely satisfactory for it involves a time-consuming process and often times leads to post-surgical problems such as infections.

In its generic process aspect then, the instant invention may be described as residing in the concept of exerting an antiandrogenic effect which comprises administering a therapeutic formulation containing as the essential ingredient, a member of the group of compounds of the general structural formula:

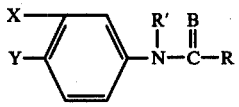

wherein X is a member of the group consisting of nitro, bromo, iodo, trifluoromethyl; Y is a member of the group consisting of hydrogen, halogen, nitro, carboxy, lower alkyl, hydroxy, lower alkoxy, polyfluoroloweralkyl, polyfluoroloweralkoxy, lower alkanoyl, lower alkanoyloxy and trifluoromethylthio, with the proviso that when Y and R' are both hydrogen, X is other than iodo; B is a member of the group consisting of sulfur and oxygen; R' is a member of the group consisting of hydrogen and alkyl having less than 5 carbon atoms and R is a member of the group consisting of isopropyl, isobutyl and branched chain alkyl having up to 8 carbon atoms.

As is true in most classes of compounds suitable for any given purposes, certain members have been found to be more desirable than others of that class. In the instant invention it is found that the preferred compounds are those compounds of formula I wherein B represents O, R' is hydrogen, and R represents isopropyl, isovaleryl and 2,3-dimethylbutyryl. Particularly, effective X and Y combinations for the foregoing are those wherein X is nitro, iodo, bromo or chloro, respectively, with Y being trifluoromethyl. Another very effective class of compounds are those wherein X is nitro and Y is either bromo or chloro. Specifically suitable compounds for the process-use aspects of this invention are: 4'-nitro-3'-trifluoromethylcyclopropylcarbanilide, 4'-nitro-3'-trifluoromethylisobutyranilide, 4'-iodo-3'-trifluoromethyl-isobutyranilide, 4'-nitro-3'-trifluoromethyl-2,3-dimethylbutyranilide, 4'-nitro-3'-trifluoromethylisovaleranilide, 4'-bromo-3'-trifluoromethylisobutyranilide, 4'-nitro-isobutyranilide, 4'-chloro-3'-trifluoromethylisobutyranilide, 3'-bromo-4'-nitroisobutyranilide, 3'-chloro-4'-nitroisobutyranilide.

It is recognized that certain anilides have been known to exert untoward side effects in their use as chemotherapeutic agents. For example, it is known that at certain doses, certain anilides will cause methemoglobin formation and sulfhemobloginemia and appropriate laboratory tests are readily available to the art to determine the dosage at which these untoward side effects will be manifest (Goodman and Gilman, 1955, MacMillan Company). It is a discovery connected with the compounds of this invention that the untoward side effects do not occur at the effective dosage range wherein the compounds exert their beneficial antiandrogenic effects and thus these compounds are extremely useful for the purposes herein described. In the determination of the dosage range at which the untoward side effects will begin to appear, standard laboratory procedures may be applied. In general, the untoward side effects, if caused by the preferred compounds of this invention, are seen at doses well above the 50 mg./kg. of body weight. However, in all instances there is a sufficient difference between the therapeutic dosage and the dosage wherein toxic manifestations are elicited and thus the compounds of this invention possess a suitable therapeutic index.

In its subgeneric concepts the instant invention relates to the application of the compounds of this invention to mammals for the treatment of benign prostatic hypertrophy, acne, hirsutism, and other androgen-dependent body malfunctions and to their use in the aforementioned veterinary application.

The active substituted anilides (I) of this invention can be administered orally in the form of tablets, capsules, elixirs, and the like or may be administered by parenteral injection. Additionally, compounds may be administered in the form of suppositories (both rectal and urethral) and lotions. In tablet form they are compounded with an inert pharmaceutical carrier which may contain a suitable binder such as, for example, gums, starches, and sugars. They may also be incorporated into gelatin capsules or formulated into elixirs which have the advantage of being susceptible to manipulations in flavor by the addition of standard natural or synthetic agents. Highly satisfactory administration may also be achieved in the form of aqueous parenteral suspension. The compounds of this invention effectively elicit an antiandrogenic effect at about 1 to about 50 mg./kg. of body weight on a daily basis. Preferably, these formulations are so proportioned as to afford a unit dosage of from about 1 to about 100 mg. of active substituted-anilide. Particularly preferred are unit dosages ranging from about 5 to about 25 mg. Preferably, the compounds are administered orally.

Furthermore, the therapeutically active ingredient may be admixed with the food of the species to which the administration is desired, thereby obtaining a therapeutically efficacious dose level.

Representative embodiments of the formulations containing the compositions of this invention are as follows:

| TABLET FORMULATIONS | |
|---|---|
| Formula A (5 mg.) | Milligrams per Tablet |
| 4'-nitro-3'-trifluoromethyl-isobutyranilide | 5.0 |
| Starch, Food Grade | 5.0 |
| Lactose, U.S.P. (Spray Dried) | 89.0 |
| Magnesium Stearate, U.S.P. | 0.5 |
| | 100.0 |
| Formula B (25 mg.) | |
| 4'-nitro-3'-trifluoromethyl-isobutyranilide | 25.0 |
| Starch, Food Grade | 10.0 |
| Lactose, U.S.P. (Spray Dried) | 164.0 |
| Magnesium Stearate, U.S.P. | 1.0 |
| | 200.0 |

Blend the milled 4'-nitro-3'-trifluoromethylisobutyranilide with the starch in a suitable mixing vessel. Add an equal weight of the spray dried lactose to the blend and mix until uniform. Combine the resultant blend with the remainder of the spray dried lactose and mix until uniform. Charge the magnesium stearate with a portion of the active tablet mix and blend. Blend the magnesium stearate mix with the remaining active tablet base. Continue mixing until uniform. Compress to target weight (100.0 mg. for 5 mg. tablet and 200.0 mg. for 25 mg. tablet).

| CAPSULE FORMULATIONS | |
|---|---|
| Formula | Milligrams per Capsule |
| 4'-nitro-3'-trifluoromethyl-cyclopropylcarbanilide | 5.0 |
| Lactose, U.S.P. (Spray Dried) | 292.0 |
| Magnesium Stearate, U.S.P. | 3.0 |
| | 300.0 |

Blend ingredients until uniformly mixed. Fill into hard gelatin capsule.

| PARENTERAL SUSPENSION | |
|---|---|
| Formula A (5 mg.) | Milligrams per Milliliter |
| 3',4'-ditrifluoromethylcyclopropylcarbanilide | 5.00 |
| Methyl Cellulose 15 cps. U.S.P. | 0.05 |
| Sodium Citrate, Dihydrate | 6.00 |
| Benzyl Alcohol, NF | 9.00 |
| Methylparaben, U.S.P. | 1.80 |
| Propylparaben, U.S.P. | 0.20 |
| Water for Injection, U.S.P. | 1.00 |
| 4'-nitro-3'-trifluoromethylisobutyranilide | 25.00 |
| Methyl Cellulose 15 cps. U.S.P. | 0.25 |
| Sodium Citrate, Dihydrate | 30.00 |
| Benzyl Alcohol, NF | 9.00 |
| Methylparaben, U.S.P. | 1.80 |
| Propylparaben, U.S.P. | 0.20 |
| Water for Injection, U.S.P. q.s. a.d. | 1.00 |

Charge 45 liters of water for injection into a suitable stainless steel vessel and heat to 85°–90° C. With vigorous agitation, slowly sprinkle the methyl cellulose into the hot water (5 mg. for formula A or 25 for formula B). Agitate until the methyl cellulose is thoroughly dispersed and wetted. Add approximately, 30 liters of cold (0°–5° C.) water for injection. Cool the entire mixture to 8° C. Dissolve the sodium citrate (600 gm. of formula A or 3000 gm. for formula B) in enough water for injection to make 5 liters of solution. Slowly and with agitation add this solution to the cooled methyl cellulose solution. Dissolve the parabens (180 gm. of methyl and 20 gm. of propyl) in 900 gm. of benzyl alcohol which has been heated to 30° C. Charge this solution to the chilled methyl cellulose solution. Bring the resulting solution to 90 liters with water for injection and agitate until uniform. In a sterile area, pass the batch through a sterile filter. Asceptically transfer about 3.5 liters of the sterile methyl cellulose solution to a separate container reserving the remainder of the batch in a sterile stainless steel mixing tank. Slurry the 4'-nitro-3'-trifluoromethylisobutyranilide in sterile colloid mill with about 2 liters of the separated methyl cellulose solution and add the slurry to the solution in the mixing tank. Rinse the slurry container and the mill with the remaining 1.5 liters of reserved methyl cellulose solution and add the rinse to the mixing tank. Rinse the slurry container and mill with 2 liters of water for injection and add the rinse to the mixing tank. Adjust the volume in the mixing tank to 100 liters with water for injection and agitate until uniform. The batch affords 100 liters of sterile suspension having the proportions of formula A or formula B.

| Formula and Method of Manufacture for 4-Nitro-3-Trifluoro-Methylisobutyranilide Capsules in 10, 25, 50, 100, 150 and 200 Mg. Dosage Units | | | | | | |
|---|---|---|---|---|---|---|
| FORMULA | MG./CAPSULE | | | | | |
| '-Nitro-3-trifluoro-methylisobutyranilide* (Milled) | 10.00 | 25.00 | 50.00 | 100.00 | 150.00 | 200.00 |
| Lactose | 375.00 | 360.00 | 335.00 | 285.00 | 235.00 | 185.00 |
| Sodium Lauryl Sulfate | 12.00 | 12.00 | 12.00 | 12.00 | 12.00 | 12.00 |
| Polyvinylpyrrolidone (PVP) | 25.00 | 25.00 | 25.00 | 25.00 | 25.00 | 25.00 |
| S.D. Alcohol, 3-A** | — | — | — | — | — | — |
| Corn Starch | 77.00 | 77.00 | 77.00 | 77.00 | 77.00 | 77.00 |

Formula and Method of Manufacture for 4-Nitro-3-Trifluoro-Methylisobutyranilide Capsules in 10, 25, 50, 100, 150 and 200 Mg. Dosage Units

| FORMULA | MG./CAPSULE | | | | | |
|---|---|---|---|---|---|---|
| Magnesium Stearate | 1.00 | 1.00 | 1.00 | 1.00 | 1.00 | 1.00 |
| Fill Weight (mg.) | 500.00 | 500.00 | 500.00 | 500.00 | 500.00 | 500.00 |

*Mixed with chunks of dry ice and passed through Fitzmill using either No. 1A or 2 screen, impact forward and fast speed. Tray and dry overnight at 40° C. (5–240 microns).
*Approximately 75 ml. 3-A alcohol/100 capsules; or 60 ml. water/100 capsules.

Method of Manufacture
1. Blend the 4-nitro-3-trifluoromethylisobutyranilide, lactose and sodium lauryl sulfate together in a suitable size mixing bowl for 20–30 minutes.
2. Pass mixed powders from Step 1 through suitable comminuting machine (Raymond Mill with Herringbone screen or Fitzmill with No. 0 screen, impact forwrd and fast speed).
3. Determine percent of milled powders recovered. Recharge milled powders to mixing bowl and blend for 5–10 minutes.
4. Dissolve polyvinylpyrrolidone in approximately 90% of the specified quantity of 3-A alcohol (or water).
5. Granulate the milled powders from Step 3 with the PVP-alcoholic solution from Step 4 using the balance of the specified 3-A alcohol as a rinse, to a uniform pasty mass (use additional 3-A alcohol if necessary).
6. Back granulate the pasty mass with corn starch, continue mixing until uniform damp granules are formed.
7. Pass damp granulation through No. 12 screen by hand (¼" screen on Fitzmill, knives forward and medium speed).
8. Spread onto trays and dry in oven for 14–16 hours at 40° C. or 50° C. for water.
9. Reduce dried granulation through No. 40 mesh screen (No. 30 mesh on Fitzmill, impact forward and fast speed).
10. Determine percent of granulation recovered.
11. Add corrected quantity of magnesium stearate and blend for 2–3 minutes.
12. Fill into capsules.

We claim:
1. A method for the treatment of acne which comprises administering to an animal having acne a therapeutically effective quantity for treating acne of a substituted anilide having the structural formula:

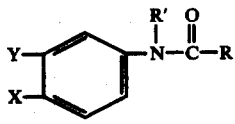

or the non-toxic pharmaceutically accceptable salts thereof, wherein X is a member selected from the group consisting of nitro, trifluoromethyl, chloro, bromo and iodo; Y is a member selected from the group consisting of hydrogen, halogen, nitro, lower alkyl, lower alkoxy, lower alkanoyl, polyfluoroloweralkoxy, polyfluoroloweralkyl, and trifluoromethylthio, with the proviso that when Y and R' are both hydrogen, X is other than iodo; R' is a member selected from the group consisting of hydrogen and alkyl having less than 5 carbon atoms, and R is cyclopropyl, cyclobutyl or branched chain alkyl having up to 8 carbon atoms.

2. A method according to claim 1 wherein R is isopropyl.
3. A method according to claim 1 wherein R is cyclopropyl.
4. A method according to claim 2 wherein X is nitro.
5. A method according to claim 3 wherein X is nitro.
6. A method according to claim 2 wherein Y is trifluoromethyl.
7. A method according to claim 3 wherein Y is trifluoromethyl.
8. A method according to claim 2 wherein R' is hydrogen, Y is trifluoromethyl and X is nitro, said compound being 4'-nitro-3'-trifluoromethylisobutyranilide.
9. A method according to claim 2 wherein R' is hydrogen, Y is trifluoromethyl and X is iodo, said compound being 4'-iodo-3'-trifluoromethylisobutyranilide.
10. A method according to claim 3 wherein R' is hydrogen, Y is trifluoromethyl, and X is nitro, said compound being 4'-nitro-3'-trifluoromethylcyclopropylcarbanilide.
11. A method according to claim 1 wherein R' is hydrogen, X is nitro, Y is trifluoromethyl and R is 3-methyl-2-butyl, said compound being 4'-nitro-3'-trifluoromethyl-2,3-dimethylbutyranilide.
12. A method according to claim 1 wherein R' is hydrogen, X is nitro, Y is trifluoromethyl and R is 2-methylpropyl, said compound being 4'-nitro-3'-trifluoromethylisovaleranilide.
13. A method according to claim 1 wherein R' is hydrogen, X is bromo, Y is trifluoromethyl and R is isopropyl, said compound being 4'-bromo-3'-trifluoromethylisobutyranilide.
14. A method according to claim 1 wherein R' is hydrogen, X is chloro, Y is trifluoromethyl and R is isopropyl, said compound being 4'-chloro-3'-trifluoromethylisobutyranilide.
15. A method according to claim 1 wherein R' is hydrogen, X is nitro, Y is bromo and R is isopropyl, said compound being 3'-bromo-4'-nitroisobutyranilide.
16. A method according to claim 1 wherein R' is hydrogen, X is nitro, Y is chloro and R is isopropyl, said compound being 3'-chloro-4'-nitroisobutyranilide.

* * * * *